United States Patent [19]

Phelps, III

[11] Patent Number: 4,821,742
[45] Date of Patent: Apr. 18, 1989

[54] CONTRACEPTIVE DEVICE

[76] Inventor: John Y. Phelps, III, 1530 N. Key Blvd., Unit 202, Georgetown Univ., Rosslin, Va. 22209

[21] Appl. No.: 134,122

[22] Filed: Dec. 17, 1987

[51] Int. Cl.$^4$ ............................................. A61F 5/42
[52] U.S. Cl. .................................... 128/842; 128/844; 604/352
[58] Field of Search ............... 604/349, 350, 351, 352, 604/353; 128/132 R, 842, 844; 206/69

[56] References Cited

U.S. PATENT DOCUMENTS

| 822,092 | 5/1906 | Woodruff | 604/352 |
|---|---|---|---|
| 824,634 | 6/1906 | Ezell | 604/351 |
| 3,085,570 | 4/1963 | Penska | 604/349 |
| 3,645,835 | 2/1972 | Hodgson | 428/480 |
| 3,677,225 | 7/1972 | Czirely | 206/69 |
| 3,951,141 | 4/1976 | Kopelowicz | 604/351 |
| 4,074,712 | 2/1978 | Wright | 604/349 |
| 4,320,752 | 3/1982 | Comparetto | 604/349 |

FOREIGN PATENT DOCUMENTS

| 0494540 | 3/1930 | Fed. Rep. of Germany | 604/349 |
|---|---|---|---|
| 1595711 | 8/1981 | United Kingdom | 604/349 |
| 2181953 | 5/1987 | United Kingdom | 604/349 |

Primary Examiner—C. Fred Rosenbaum
Assistant Examiner—Mario Costantino
Attorney, Agent, or Firm—Armstrong, Nikaido, Marmelstein & Kubovcik

[57] ABSTRACT

A condom comprising a semi-spherical shaped body for covering the glans penis of a male sex organ and leaving the corona surrounding the glans penis exposed and forming a fluid tight enclosure over the opening of the glands penis, the condom on the surface to be applied to the surface of the glans penis having a pressure sensitive adhesive coating, the coating extending around the peripheral area of such surface, an adhesive free area on such surface for positioning over the glans penis opening and free areas of adhesive extending radially outward therefrom.

6 Claims, 2 Drawing Sheets

Fig. 4

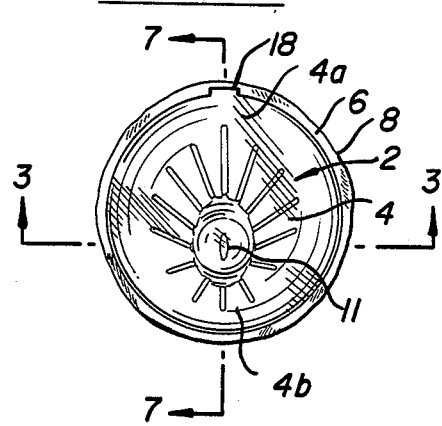
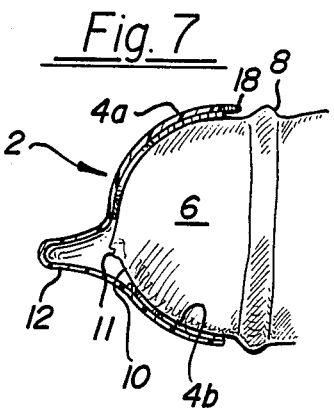
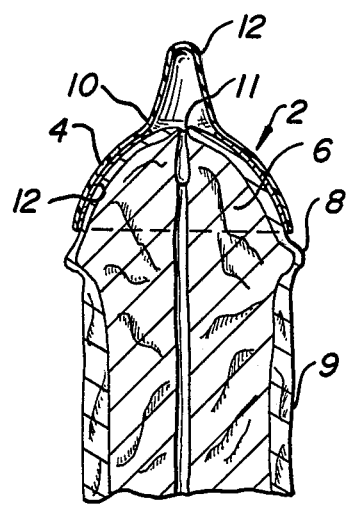
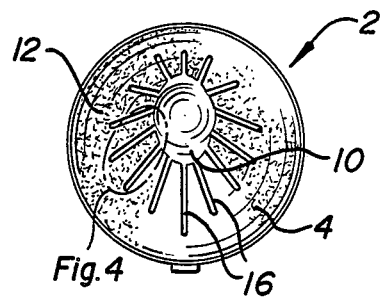
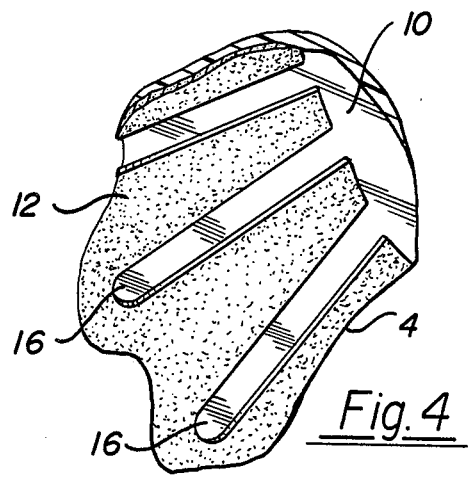

CONTRACEPTIVE DEVICE

This invention relates to a condom device, more particularly, a condom device for preventing spread of venereal disease, including AIDS, which has become an important problem in today's society.

The use of condoms for preventing the spread of venereal disease, such as, gonorrhea, trichomonas, chlamydia, and the like, spread by the female to the male through the moist mucosa of the external meatus of the male sex organ and by the male to the female through the male semen is well known and has been used for such purpose, as well as contraceptive purposes, for many years. However, because of partial loses of sexual pleasures when such devices are used and because pharmaceutical and medical procedures have been developed for the treatment of such diseases, most often such devices have not been used. More recently, the discovery and spread of a disease, come to be known as auto immune deficiency syndrome, or AIDS, where pharmaceutical and medical procedures for treatment are unknown, have made the use of condoms, where there is likelihood of spread of AIDS, of substantial importance. Despite such importance, use of condoms has continued to be hampered because of the partial loses of sexual pleasures.

Attempts have, heretofore, been made to overcome at least some of the loses of sexual pleasures in the use of such devices by reducing the area of the male penis covered by the device. One such attempt is shown and described in U.S. Pat. No. 3,677,225, dated July 18, 1972, devised long before AIDS and its spread had become widely known.

In the arrangement of such '225 patent, the closed or semispherical seminal receiving end of the device, of a flexible material, such as rubber, is joined at the opposite or open end in an outwardly extending perforated flange coated on its inner surface with a pressure-sensitive adhesive coating. The device of such patent is applied to the end of a male sex organ by the adhesive and is removed by mechanical separation as by the use of a liquid or creamy solvent which penetrates through the perforations. The outwardly extending perforated flange of the device of the '225 patent is flat. Thus, to apply such device to the end of the male sex organ, the adhesive area must be stretched and shaped as it is applied. Such stretching and shaping makes application difficult and detracts from the comfort of the device in its use. The condom device of the '225 patent is annular which makes application of the device of such patent difficult because it does not provide for the asymmetry of the glans penis.

In the instant invention, a condom is provided which is applied to the glans penis of the male sex organ leaving the corona of the glans penis, the most sensitive area, exposed. The surface of the condom to be applied to the glans penis is coated with a pressure sensitive adhesive compatible with the glans penis surface and adhesive thereto, such as the adhesive compositions disclosed and described in U.S. Pat. No. 3,645,835 as adhesive compositions A to E and combinations and modifications thereof, which disclosure and description is incorporated herein by reference. The area of the surface to be applied over the opening or external meatus, an area there around and areas radiating outwardly and opening at one end into such adhesive free area are also left free of adhesive. Thus, the areas between such radiating adhesive free areas and the area at the periphery of the contact area and extending continuously around such peripheral area is adhesively coated. The adhesive strength of the adhesive extending continually around the peripheral area may be stronger than the adhesive extending between the radially extending adhesive free areas.

Upon initial discharge, semen is a thick viscous secretion but, within minutes because of its own enzymatic action, breaks down into a nonviscous liquid. Such nonviscous liquid will readily flow into the adhesive free areas extending radially from the adhesive free area at the opening or external meatus from which the thick viscous secretion emerges. The pressure sensitive material may be of a nature that it is soluble in the nonviscous fluid.

The adhesive, in the pattern described above, may be applied to the surface of the condom to be contact by the glans penis surface by printing, stenciling, masking or other suitable method and is applied so as to maximize the utilization of the surface to which the condom is to adhere. That is, because there is less surface area on the glans penis from the external meatus to the corona of the glans penis on the vertical side than on the dorsal side, more adhesive area surface is provided on the dorsal side, than on the ventral side.

The instant invention will be more fully described and will be better understood from the following description of preferred embodiments of the invention, taken with the appended drawings, in which:

FIG. 1 is a top view of the device of the instant invention showing the device as applied to the glans penis;

FIG. 2 is a bottom view of the device of FIG. 1;

FIG. 3 is a section taken at 3—3 FIG. 1;

FIG. 4 is an enlarged view of the section at 4, FIG. 2;

FIG. 7 is a partial sectional view taken at 7—7, FIG. 1.

Figure 5:
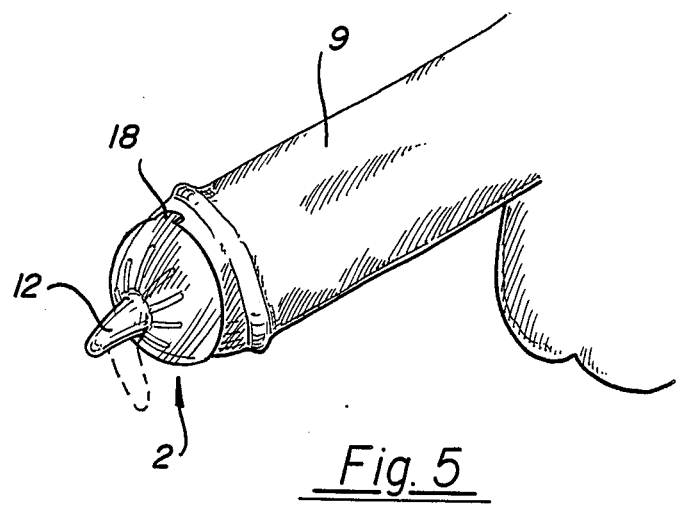
FIG. 5 is a perspective view of the embodiment of the device of the instant invention shown in FIG. 1-4 and 7.

Referring, first, to FIGS. 1-5 and 7, the condom of the instant invention, generally designated 2, includes a base 4 of flexible, stretchable material, such as rubber for application to a glans penis 6, having a corona 8, a shaft 9 and an external meatus, or opening 11. For purposes which will be later described, condom 2 has an area 10 for positioning over and around external meatus 10 and a pocket or reservoir 12 extending from area 10, all integral with base 4.

Except for outwardly extending pocket 12, formed integrally with base 4, base 4 is of substantially semispherical shape and is coated on its inner surface with a pressure sensitive adhesive 14, leaving the inner surface of area 10, pocket 12 and stripe areas 16, radiating outwardly from area 10, and open at one end thereto, free of adhesive. As best shown in FIGS. 1, 5 and 7, the top or dorsal side 4a of condom 2 is longer than the bottom or ventral side 4b. At the top or dorsal side, base 4 is provided with a tab 18 formed integral with base 4 and extending outwardly therefrom. Preferably, the inner surface of tab 18 is uncoated with adhesive and, in addition to providing a means for peeling the condom 2 from the glans penis after use, provides a ready reference for locating the longer dorsal on top side 4a of base 4 for applying the condom to the glans penis.

Figure 6:
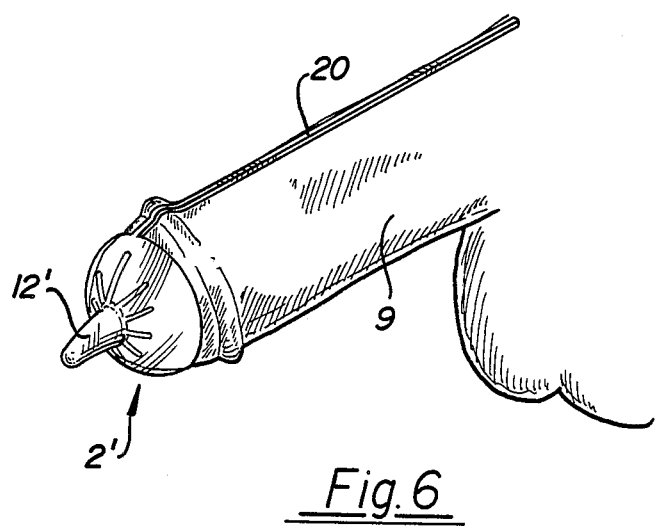
FIG. 6 is a perspective view of another embodiment of the invention.

As best shown in FIG. 6, in another embodiment of the invention, tab 18 is replaced with elongated tab 20 which functions the same as tab is but lays along shaft 9 when such condom 2' is in use.

For purposes of storage and handling, the adhesive coating is covered with, for example, a coated paper strip which can be readily peeled off of the adhesive coated surface without the removal or damage to the adhesive or the adhesive coated surface. Such coated strips, as is the usual practice with pressure sensitive adhesive coated articles, prevents such article from sticking to the package container, other articles, or other surface before the condom is prepared for use.

The terms and expressions which have been employed in the foregoing description are used as terms of description and not of limitation, and there is no intention, in the use of such terms and expressions, of excluding any equivalents of the feature shown and described or portions thereof, but is recognized that various modifications are possible within the scope of the invention claimed.

What is claimed:

1. A condom for adhesive attachment to the glans penis of a male sex organ, said condom comprising a semispherical shaped body for substantially covering said glans penis and leaving the corona surrounding said glans penis exposed, said condom forming a fluid enclosure over the opening of the glans penis and the area therearound, said condom on the surface thereof to be applied to be surface of the glans penis having a pressure sensitive adhesive coating, said adhesive coating being continuous around the peripheral area of said surface for forming a fluid tight seal with said glans penis, said surface to be applied having an adhesive free area surrounded by said adhesive coating for positioning over said glans penis opening for forming a fluid reservoir between said glans penis and said condom, said adhesive free area including adhesive free strips radiating outward from said adhesive free area, said strips opening at their adhesive free area end into said adhesive free area and being closed at their opposite end by the continuous adhesive coating around said peripheral area.

2. A condom, as recited in claim 1, in which said peripheral area coating at one side of the periphery of said surface is larger that the area coated at the other side of said the periphery of surface.

3. A condom, as recited in claim 2, in which said condom has a tab extending outwardly from the peripheral edge of said body at the area where said peripheral area coated is larger.

4. A condom, as recited in claim 3, in which said tab is of extended length for extension axially along the penis shaft when said condom is applied to the glans penis.

5. A condom, as recited in claim 1, in which said condom has a tab extending outward from the peripheral edge of said body.

6. A condom, as recited in claim 5, in which said tab is of extended length for extension axially along the penis shaft when said condom is applied to the glans penis.

* * * * *

UNITED STATES PATENT AND TRADEMARK OFFICE
CERTIFICATE OF CORRECTION

PATENT NO. : 4,821,742

DATED : April 18, 1989

INVENTOR(S) : John Y. PHELPS, III

It is certified that error appears in the above-identified patent and that said Letters Patent is hereby corrected as shown below:

On the cover page, Item [76], delete "Georgetown Univ.,".

Signed and Sealed this

Third Day of April, 1990

Attest:

HARRY F. MANBECK, JR.

*Attesting Officer*  *Commissioner of Patents and Trademarks*